United States Patent [19]

Munari et al.

[11] Patent Number: 4,559,063
[45] Date of Patent: Dec. 17, 1985

[54] MULTI PURPOSE ON COLUMN INJECTION

[75] Inventors: Fausto Munari; Giovanni Ostan; Carlo Saravalle, all of Milan; Bruno Tosi, Verano Brianza, all of Italy; Sorin Trestianu, Brussels

[73] Assignee: Carlo Erba Strumentazione S.p.A., Rodano, Italy

[21] Appl. No.: 648,220

[22] Filed: Sep. 7, 1984

[30] Foreign Application Priority Data

Sep. 9, 1983 [IT] Italy ............... 22875/83[U]
Jun. 29, 1984 [IT] Italy ............... 22432/84[U]

[51] Int. Cl.$^4$ ............................................. B01D 15/08
[52] U.S. Cl. ........................................ 55/67; 55/197; 55/386; 436/161
[58] Field of Search ................... 55/67, 197, 386; 73/23.1 C, 61.1 C, 863.11, 863.12; 210/175, 656, 198.2; 436/161

[56] References Cited

U.S. PATENT DOCUMENTS

| | | | |
|---|---|---|---|
| 3,063,286 | 11/1962 | Nerheim | 73/23.1 |
| 3,230,046 | 1/1966 | Beroza | 436/161 X |
| 3,244,152 | 4/1966 | Mixon et al. | 55/67 X |
| 3,401,552 | 9/1968 | Ruchelman | 73/23.1 |
| 3,401,565 | 9/1968 | Stoll et al. | 73/863.11 |
| 3,463,012 | 8/1969 | McKinney et al. | 73/863.11 |
| 3,592,046 | 7/1971 | Cramers et al. | 73/23.1 |
| 4,035,168 | 7/1977 | Jennings | 55/197 X |
| 4,269,608 | 5/1981 | Sisti et al. | 55/67 |
| 4,383,839 | 5/1983 | Sisti et al. | 55/67 |
| 4,414,857 | 11/1983 | Brazhnikov et al. | 73/863.11 |
| 4,422,860 | 12/1983 | Feinstein | 55/67 |

Primary Examiner—Robert Spitzer
Attorney, Agent, or Firm—Millen & White

[57] ABSTRACT

The invention relates to a direct on column non-vaporizing injector for gas chromatographic analyses and comprising an accessory device capable of allowing injection with sample vaporization and possible splitting. The accessory device is formed by a tubular element which, at one end, can be fixed to the injector body coaxially to the passage for the injection syringe needle, while its opposite end is closed by an insert provided with an axial hole in which the gas chromatographic capillary column head is pneumatically inserted, said insert being provided with at least one other hole for splitting the vaporized sample. The tubular element houses a vaporization tube which under conditions of thermal exchange with heating means, is pneumatically connected to said passage for the injection syringe needle and to said insert holes and receives the upper end of the gas chromatographic column. Gas is employed countercurrently to strip off undesired components while the liquid sample is held in the vaporization chamber.

23 Claims, 3 Drawing Figures

4,559,063

MULTI PURPOSE ON COLUMN INJECTION

BACKGROUND OF THE INVENTION

1. Field of the Invention

This invention relates to an injector for the injection of samples to be analyzed in a gas chromatographic capillary column and, more precisely, to an injector of the non vaporizing direct on-column type, comprising an accessory device applicable thereof to allow its use also to perform injections of the vaporizing type with undilutable samples or concentrated solutions requiring a splitting of the vaporized sample, as well as to eliminate the solvent before the sample is transferred to the capillary column.

2. Description of the Prior Art

In U.S. Pat. No. 4,269,608 assigned to the same assignee, there is described an injector which can perform the injection of samples to be analyzed without vaporization, directly in the gas chromatographic column.

Said injector comprises a duct for the introduction of the injection syringe needle which can be closed by means of a valve, the lower section of said duct housing the end of a gas chromatographic column.

Said gas chromatographic column end is pneumatically connected to the duct thanks to an O-ring kept in position by a small tube coaxial to the column and screwed to the injector body. This small tube, according to what is described and claimed in the aforementioned patent, forms a jacket around the column head and the hollow space between the jacket and the column is fed with a fluid at a controlled temperature.

From U.S. Pat. No. 4,383,839 there is also known a method for the injection with vaporization of a liquid sample in a gas chromatographic capillary column comprising the steps of (a) injecting the liquid sample into the initial part of a sample vaporization tube which does not contain a stationary liquid phase (or contains an immobilized phase), the sample being kept liquid during the whole injection process;

(b) heating the vaporization tube and feeding it with carrier gas to entrain the vaporized sample;

(c) diverting part of the resulting mixture of vaporized sample and carrier gas by means of a splitter and sending the remaining part to a gas chromatographic column containing a stationary liquid phase for chromatographic separation.

The vaporization tube can be empty or a fiberglass sponge can be placed in it to hold the sample when it is in the liquid state and to release it when it passes to the vapour state. In fact, the fiberglass sponge is impermeable to the sample at the liquid state, while it is permeable to the sample when the letter is at the vapour state.

OBJECTS OF THE INVENTION

An object of this invention is now to provide an injector of the non-vaporizing direct on-column type, for instance such as the one described and illustrated in the aforementioned U.S. Pat. No. 4,269,608 and comprising an accessory device which allows said injector to be used to perform a method of the type described and claimed in the aforementioned U.S. Pat. No. 4,383,839.

Another object of the present invention is to provide an injector with an accessory device having the above-mentioned features, which is capable of holding inside the vaporization tube the sample at the liquid state and of releasing it when it passes to the vapour state, even in the case of very polar samples, for which the use of said fiberglass sponges could involve drawbacks due to their high surface and the difficulty of completely de-activating them.

Another object of this invention is to provide an injector with an accessory device of the aforementioned type, which allows the elimination, during the injection stage and in any case before the vaporization stage, of the volatile components present in a sample to be analyzed, thus allowing it only the heavy components in the sample to be analyzed.

SUMMARY OF THE INVENTION

Said objects are achieved by an on-column type injector with accessory device which comprises a tubular element, one end of which can be fixed to the injector body coaxially to the duct for the passage of the injection syringe needle, while the opposite accessory device end is closed by an insert provided with an axial hole, in which the head of a capillary gas chromatographic column is pneumatically housed, and with a hole for controllaby splitting the vaporized sample, the tubular element housing a vaporization tube under conditions of thermal exchange with heating means and which is pneumatically connected to said passage for the injection syringe needle and to said holes of the insert.

In particular, the vaporization tube can have a series of inner protrusions, turned towards the axis of the tube itself and reciprocally offset and opposed in such a way as to hold the sample when it is at the liquid state.

Moreover, the end of said tubular element in which the gas chromatographic column head in inserted, can have, besides the hole necessary to perform the vaporized sample splitting, a second hole communicating with a duct connected, through a valve, to a carrier gas line. Said duct can moreover be connected, downstream of said valve and by means of a fitting provided with an adjustable neck, to the duct for the introduction of the sample carrier gas, while the valve can be a three-way valve, allowing a selective connection of the carrier gas line to the duct for carrier gas introduction into the on-column injector or to the duct leading to the tubular element.

Thanks to the aforementioned second hole in the tubular element, during the injection of the sample to be analyzed and in any case before the vaporization stage of the sample portion to be transferred to the capillary column, it is possible to introduce carrier gas into the tubular element through said second hole and in such a way to contact strike the sample with a gas current flowing in the opposite direction to that of the sample introduction in the gas chromatographic column, said gas current carrying the sample volatile substances out of the on-column injector by means of a suitable discharge duct provided in the injector body and equipped with cut off and control valves.

The invention will be now described more in detail with reference to the attached drawings.

DESCRIPTION OF THE PREFERRED EMBODIMENTS

Figure 1:
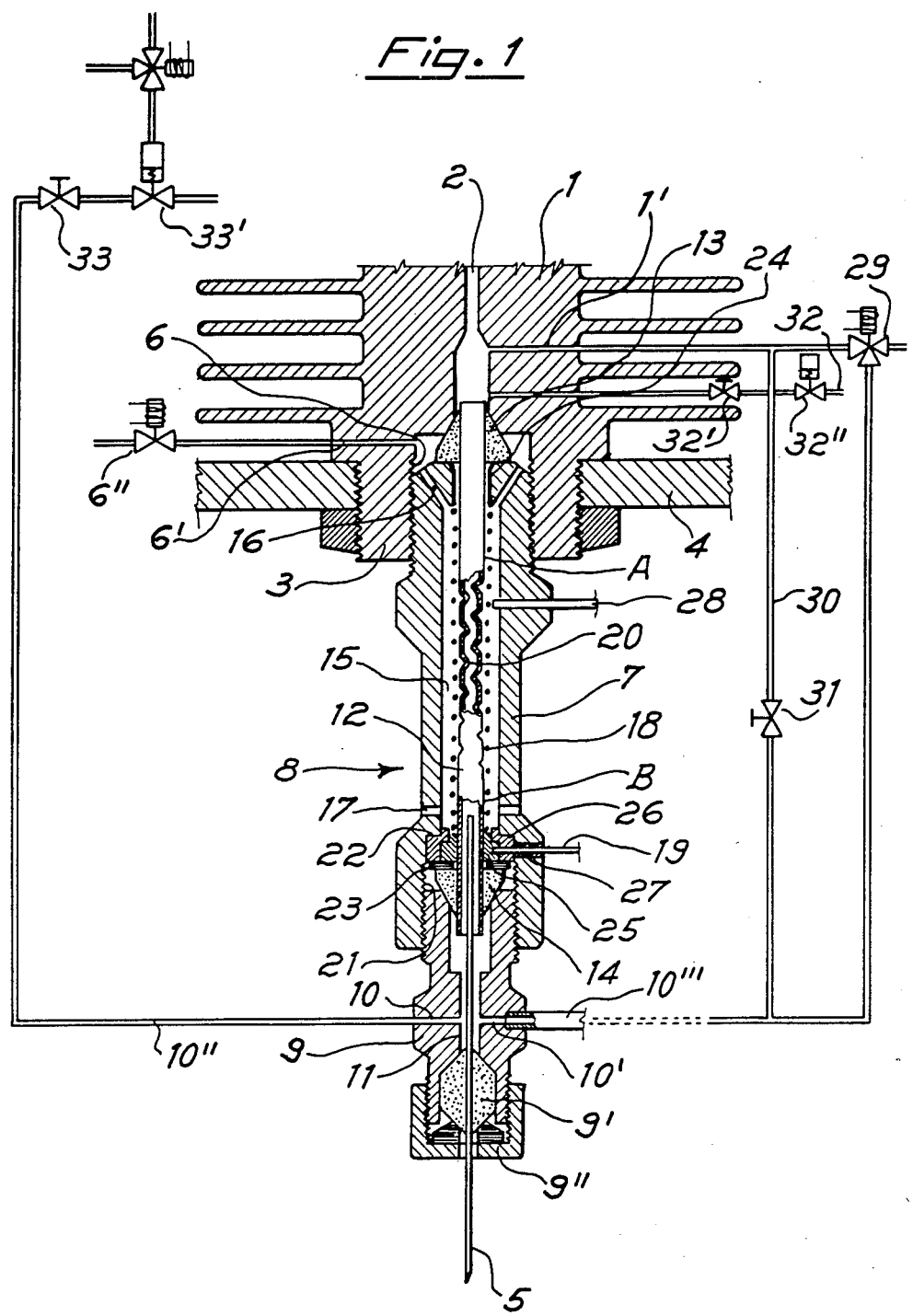
FIG. 1 is a cross-sectional view of an on-column injector equipped with a vaporization accessory device and provided with a system for the elimination of the volatile components present in the sample to be analyzed.

Referring to FIG. 1, the injector 1, for example such as the one described and illustrated in the aforementioned U.S. Pat. No. 4,269,608 comprises a duct 2, which can be closed by a valve, capable of allowing the passage of the injection syringe needle, and a duct 1' for the introduction of carrier gas. The lower part of the injector comprises a protruding body 3 coaxial to the duct 2 allowing the injector to be fixed to the walls 4 of an oven which houses a gas chromatographic capillary column 5, in particular preferably made of fused silica.

The protruding body 3 has a threaded cavity 6 coaxial to the duct 2 and into which said duct 2 and a duct 6' open, the latter duct communicating with a fluid source at controlled temperature, for example, even if not exclusively, air, possibly controlled by a valve 6''.

In the known embodiment, a small tube coaxial to the initial part of the column is screwed in the threaded cavity 6, forming a collecting chamber for the fluid at controlled temperature coming from the duct 6'.

According to the invention, in said threaded cavity 6, an accessory device 8 formed by a tubular element 7 is screwed instead of said small tube; in the lower end of said tubular element 7 is screwed an insert 9 provided with two radial holes 10 and 10' and with an axial hole 11, wherein the gas chromatographic column head 5 is inserted and pneumatically sealed and mechanically locked by a gasket 9' and a locking nut 9''.

Inside the tubular element 7, a vaporization tube 12 is positioned, the upper end of which is inserted in the duct 2 of the injector and pneumatically sealed by means of an O-ring 13 pressed against the injector body by the tubular element itself. The lower end of tube 12 is inserted in the axial hole 11 of insert 9 and pneumatically sealed by means of a gasket 14. In particular, the lower end of tubular element 7 has a threaded cavity 21 provided with a shoulder 22 capable of holding a washer 23 made of insulating material, for instance Vespel (registered trade mark), against which the gasket 14 is pushed by the insert 9.

The first of the two radial holes 10 and 10' of insert 9 communicates with a duct 10'' and is designed to allow splitting of the vaporized sample, while the second hole 10' communicates with a duct 10''' connected, through a three-way valve 29 to which the duct 1' is also connected, to a source of carrier gas. Moreover, the ducts 1' and 10''' can be connected to one another, downstream via the valve 29, by a duct 30 provided with an adjustable neck 31.

The inner part of the vaporization tube 12 can house a fiberglass sponge, or it can be provided, in an intermediate section between a point A downstream of the injection point and a point B upstream of the open end of column 5, with a series of protrusions 20 turned towards the axis of the tube itself and reciprocally offset and opposed, in a way as to create a zigzag passage for the injected sample. The protrusion 20 hold the sample inside the tube 12 when the sample is in the liquid state so as to prevent it from penetrating into the gas chromatographic column before it is vaporized.

Between the inner side walls of tubular element 7 and the vaporization tube 12 there is an hollow space 15 communicating through one or more holes 16, with said cavity 6 and therefore with duct 6' leading to the cavity itself and, through one or more holes 17, with the oven chamber, in a way as to submit the vaporization tube 12 to the controlled thermal action of the fluid introduced in 6' and discharged in 17. Said fluid is generally intended for cooling the tube 12, but it is also possible to introduce hot fluid for sample vaporization. However, for the latter purpose, it is more advisable, as illustrated, to use an electric resistor 18, wound around the tube 12 and having an end soldered to a small metal cylinder 24, soldered on its turn in the upper axial passage of element 7. The other end of resistor 18 is soldered to a small metal cylinder 25 fixed between the ring 23 and a shaped insulating gasket 26. Said cylinder 25 is connected to a first electrode 19 passing through body 7 by means of an insulating gasket 27, while the other electrode 28 is grounded in a point whatever.

Finally the injector body 1 has a third duct 32 for discharge, which is inserted in the duct 2 upstream the vaporization tube 12 and has a first valve 32' for controlling the discharge flow rate and a second valve 32'' to control the duct opening and closure.

The tubular element 7 is fixed to the injector 1 and the gas chromatographic column head is connected, through insert 9, to the vaporization tube 12, in particular it is inserted with its free end straight into the lower part of the vaporization tube 12.

Figure 2:
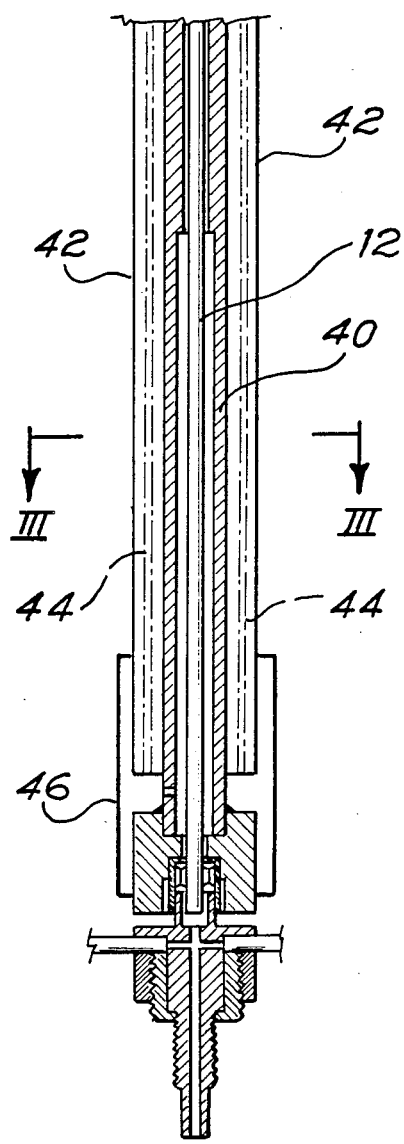
FIG. 2 is a cross-sectional view of a modified embodiment of the vaporization accessory device according to the invention.
Figure 3:
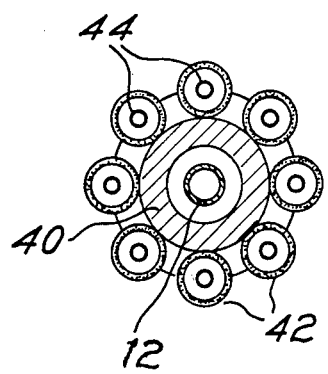
FIG. 3 is a section taken along the line III—III of FIG. 2.

FIGS. 2 and 3 show another embodiment of the invention, wherein the vaporization tube 12 is housed in a tubular element 40 in a material adapted for heat transfer, for instance in a metallic material. This tubular element is heated by a plurality of resistors 44 housed in tubular insulating sheats 42. To heat the splitting point, which is a very important feature, a liner 46 made of aluminum, or any other direct or indirect heating means can be provided for.

To perform an injection with or without elimination of the volatile components (back-flush), the following operations must be accomplished.

The valve (not illustrated) to open and close duct 2 of the injector is opened and the upper part of the vaporization tube 12 receives through the duct 2 the injection syringe needle containing a sample to be analyzed which is at the liquid state.

The sample is injected into the tube 12, the syringe needle is removed and the valve controlling the duct 12, is closed. The fiberglass sponge inserted in the tube 12 or the protrusions 20 on the tube wall prevent the sample at the liquid state from penetrating into the column 5. On the other hand, during injection the temperature of tube 12 is kept at such a value as to prevent sample vaporization by means of cooling fluid introduced in 6' and discharged in 17. If required, the tube 12 may be heated to a controlled temperature to eliminate by the back flush or splitting line well defined light sample components not interesting for the analysis.

At this point, after eventual interruption or communication of cooling, the vaporization tube 12 is heated at a chosen temperature, for instance by the electric resistor 18, until the sample is completely vaporized. The carrier gas which flows into the injector duct 2, coming from duct 1, enters the vaporization tube 20 and sweeps the vaporized sample towards the chromatographic column. Part of the mixture formed by the vaporized sample and the carrier gas can be deviated outside the column 5 and discharged through the duct 10 of insert 9 so that the column receives only a certain amount of vaporized sample. In particular, the ratio between the amount of mixture deviated by the duct 10 (splitting ratio) is determined by controlling the flow rate in said duct and the opening or closing of same through the control valve 33 and cut off valve 33' connected to the duct 10, according to the temperature of tube 12. Of course, a splitless injection can be made by closing valve 33'.

At the end of the analysis, in order to rapidly cool the tube 12, a cooling gas, for example ambient air, is introduced into the hollow space 15 of the tubular element. Said gas, after heat exchange contact with the tube 12, flows into the oven chamber through holes 17 provided in the lower part of the tubular element.

In case the sample to be analyzed contains volatile substances which must not enter the gas chromatographic column, during the sample injection stage and before the sample vaporization, the duct 10''' is fed with inert gas. In more detail, when the syringe needle to inject the sample has been introduced into the duct 2, the valve 29 is regulated in such a way that only the duct 10''' communicates with the inert gas source, the valve 31 is regulated in such a way that the duct 10''' is connected to the duct 1' while the valve 32'' of the discharge duct is open. The carrier gas sent to the duct 10''' comes out from the hole 10' of the insert 9, partly penetrating into the gas chromatographic column and partly into the tube 12.

A small fraction of carrier gas introduced in the duct 10''' passes through the duct 30 and the neck 31 and flows into the duct 1'. At this point the sample is injected into the tube 12 where it meets the opposite inert gas current coming in through the duct 10'''; in this way the more volatile substances present in the sample are swept by the carrier gas towards the opposite direction to that of sample introduction into the gas chromatographic column and sent out of the injector through duct 32 and under the control of valve 32', for example a needle valve. The small fraction of inert gas coming out from the duct 1' prevents the volatile substances from entering the duct 1' itself.

The heaviest part of the sample is held by the protrusions 20 of tube 12 when contacted by the carrier gas flow coming from hole 10' of insert 9 and entraining the sample volatile substances. When this stage of elimination of the more volatile substances present in the sample is over and the sample vaporization stage begins, the valve 29 is regulated in such a way that the carrier gas flows only into the duct 1' and the valve 32'' of the discharge duct is closed. The duct 10''' is kept in communication with duct 1' so that a fraction of carrier gas flowing to the duct 1' comes out from the radial hole 10' of the insert 9 preventing the vaporized sample from entering the duct 10'''.

The adjustable neck 31 is designed to control the gas flow rate necessary to create a fluid seal, alternatively in the duct 1' during the stage of elimination of the volatile substances present in the sample, and in the radial hole 10' during the vaporization stage and the sample injection in the gas chromatographic column.

We claim:

1. A method of injecting a liquid sample into a gas chromatographic capillary column, comprising the steps of:
   (a) injecting a liquid sample into the inlet of a vaporization tube, (b) passing a carrier gas into the outlet of the vaporization tube and volatilizing components of the liquid which are not desired to be submitted to the chromatographic analysis, and removing said carrier gas and said undesired components from a discharge conduit proximate the inlet of said vaporization tube, (c) heating the vaporization tube to volatilize the remaining liquid components and passing a carrier gas to the inlet of the vaporization tube to entrain the resultant vaporized liquid sample, and (d) passing resultant gas to a gas chromatographic column to conduct the gas chromatographic separation of the gaseous mixture.

2. A method according to claim 1, wherein the resultant mixture of carrier gas and vaporized sample constitutes a quantity in excess of the capacity of the capillary chromatographic column, and comprising the further step of splitting the resultant excess away from the column.

3. A method of passing a gas into a gas chromatographic column comprising the steps of:
   (a) passing a liquid sample into a vaporization tube and maintaining the temperature of the vaporization tube below the boiling point temperature of to-be-analyzed components in the sample during said passing to avoid flash evaporation of said components;
   (b) heating said vaporization tube to vaporize the sample;
   (c) passing the vaporized sample into said gas chromatographic column; and
   (d) cooling the vaporization tube.

4. A method according to claim 3, wherein the cooling of the vaporization tube comprises passing a cooling fluid in indirect heat exchange contact with walls of said vaporization tube.

5. A method according to claim 4, wherein said passing of said cooling fluid is conducted in both of steps (a) and (d).

6. A method according to claim 4, wherein said heating comprises converting electrical energy to heat adjacent said walls of said vaporization tube.

7. A method according to claim 3, wherein in step (a), said vaporization tube is cooled.

8. A direct on column non-vaporizing injector for gas chromatographic analyzers, comprising an injector body, an accessory device for vaporization injections in the form of a tubular element having two ends and internal sidewalls, one end of said tubular element being fixable to the injector body coaxially to an injector passage adapted for the insertion of an injection syringe needle, the other end of said tubular element being closed by an insert provided with an axial hole and at least one other hole for vaporization sample splitting, a gas chromatographic capillary column being inserted and pneumatically sealed in said axial hole, heating means for heating a vaporization tube housed within said tubular element, said vaporization tube being connected to said injector passage for the injection syringe needle and to said holes of said insert, and receiving the upper end of the gas chromatographic column, said vaporization tube being provided with an inner section having a series of protrusions turned towards the axis of the tube and reciprocally offset and opposed for holding the injected sample in a liquid state.

9. An injector according to claim 8, wherein the end of said tubular element in which the gas chromatographic column is inserted presents, besides said hole for the vaporized sample splitting, a second hole communicating with a first duct connected, through a valve, to a source of carrier gas.

10. An injector according to claim 9, wherein said first duct is connected, downstream of said valve and by means of a second duct provided with an adjustable neck, to a third duct for the introduction of carrier gas into the on-column injector.

11. An injector according to claim 10, wherein the injector body has, between the upper end of the vaporization tube and said third duct for the introduction of carrier gas, a fourth discharge duct from the passage for the syringe needle and controlled by a valve system.

12. An injector according to claim 11, wherein the valve system includes a needle valve controlling the discharge flow rate and a cut off valve.

13. An injector according to claim 10, wherein the injector body has, between the upper end of the vaporization tube and said third duct for the introduction of carrier gas, a fourth discharge duct from the passage for the syringe needle, said discharge duct being provided with valve means for controlling fluid flow within said duct.

14. A direct on column non-vaporizing injector for gas chromatographic analyzers, comprising an injector body, an accessory device for vaporizing injections in the form of a tubular element having two ends and internal sidewalls, one end of said tubular element being fixable to the injector body coaxially to an injector passage for an injection syringe needle, the other end of said tubular element being closed by an insert, said insert being provided with an axial hole and at least one other hole adapted for vaporization sample splitting, a gas chromatographic capillary column being inserted and pneumatically sealed in said axial hole, heating means for heating a vaporization tube housed in said tubular element, said vaporization tube being in communication with said injector passage for the injection syringe needle and, with said holes of said insert and receiving the upper end of the gas chromatographic column, there being free space between said upper end of said column and said vaporization tube to allow communication between the gas chromatographic column and the vaporization tube and to form a passageway externally of said chromatoraphic column for communication between the vaporization tube and said at least one other hole adapted for vaporization sample splitting, and a hollow space between the internal sidewalls of said tubular element and said vaporization tube, said space being adapted to communicate with a source of cooling fluid at a controlled temperature whereby the vaporization tube can be cooled prior to the introduction of the sample.

15. An injector according to claim 14, said vaporization tube being provided with an inner section having a series of protrusions turned towards the axis of the tube and reciprocally offset and opposed for holding the injected sample in a liquid state.

16. An injector according to claim 15, wherein the upper end of said tubular element is shaped in such a way as to match with the cavity of the injector body, coaxial to the column and forming a collecting chamber for heat transmission fluid.

17. An injector according to claim 14, wherein the end of said tubular element in which the gas chromatographic column is inserted presents, besides said hole for the vaporized sample splitting, a second hole communicating with a first duct connected, through a valve, to a source of carrier gas.

18. An injector according to claim 17, wherein said first duct is connected, downstream of said valve and by means of a second duct provided with an adjustable neck, to a third duct for the introduction of carrier gas into the on column injector.

19. An injector according to claim 18, wherein the injector body has, between the upper end of the vaporization tube and said third duct for the introduction of carrier gas, a fourth discharge duct from the passage for the syringe needle and controlled by a valve system.

20. An injector according to claim 19, wherein the valve system includes a needle valve controlling the discharge flow rate and a cut off valve.

21. An injector according to claim 14, said insert being elongated, said at least one other hole adapted for vaporization sample splitting being disposed substantially downstream of said vaporization tube.

22. An injector according to claim 14, wherein said hollow space communicates at one end with an injector duct adapted to be connected to a said source of cooling fluid at a controlled temperature and, at the opposite end, with space external of said injector whereby fluid heated during cooling of the vaporization tube can be withdrawn from the injector.

23. An injector according to claim 22, wherein the upper end of said tubular element is shaped in such a way as to match with the cavity of the injector body, coaxial to the column and forming a collecting chamber for the cooling fluid.

* * * * *